US008263636B2

(12) United States Patent
Ansorge et al.

(10) Patent No.: US 8,263,636 B2
(45) Date of Patent: Sep. 11, 2012

(54) DUAL ALANYL AMINOPEPTIDASE AND DIPEPTIDYL PEPTIDASE IV INHIBITORS FOR FUNCTIONALLY INFLUENCING DIFFERENT CELLS AND FOR TREATING IMMUNOLOGICAL INFLAMMATORY, NEURONAL AND OTHER DISEASES

(75) Inventors: Siegfried Ansorge, Hohenwarthe (DE); Ute Bank, Stassfurt (DE); Karsten Nordhoff, Magdeburg (DE); Michael Taeger, Heinrichsberg (DE); Frank Striggow, Gerwisch (DE)

(73) Assignees: IMTM GmbH, Magdeburg (DE); Keyneurotek Pharmaceuticals AG, Magdeburg (DE)

( * ) Notice: Subject to any disclaimer, the term of this patent is extended or adjusted under 35 U.S.C. 154(b) by 1365 days.

(21) Appl. No.: 10/575,878

(22) PCT Filed: Oct. 15, 2004

(86) PCT No.: PCT/EP2004/011644
§ 371 (c)(1),
(2), (4) Date: Sep. 15, 2006

(87) PCT Pub. No.: WO2005/034940
PCT Pub. Date: Apr. 21, 2005

(65) Prior Publication Data
US 2007/0078130 A1    Apr. 5, 2007

(30) Foreign Application Priority Data

Oct. 15, 2003  (DE) .................................. 103 48 044

(51) Int. Cl.
*A61K 31/4045*     (2006.01)
*C07D 209/08*      (2006.01)
(52) U.S. Cl. ........................................ 514/412; 548/452
(58) Field of Classification Search .................. 548/452; 514/412
See application file for complete search history.

(56) References Cited

U.S. PATENT DOCUMENTS

| 6,090,250 | A | 7/2000 | Mazzeo et al. | |
|---|---|---|---|---|
| 6,410,584 | B1 * | 6/2002 | Pamukcu et al. | ............. 514/416 |
| 6,429,212 | B1 | 8/2002 | Hashimoto | |
| 2002/0198205 | A1 | 12/2002 | Himmelsbach et al. | |
| 2004/0132639 | A1 | 7/2004 | Ansorge et al. | |
| 2004/0138214 | A1 | 7/2004 | Himmelsbach et al. | |
| 2004/0147434 | A1 | 7/2004 | Ansorge et al. | |
| 2005/0004205 | A1 | 1/2005 | Evans et al. | |
| 2005/0014699 | A1 | 1/2005 | Ansorge et al. | |
| 2005/0070482 | A1 | 3/2005 | Bachovchin | |
| 2005/0113310 | A1 | 5/2005 | Striggow et al. | |
| 2006/0040850 | A1 | 2/2006 | Ansorge et al. | |
| 2006/0211602 | A1 | 9/2006 | Ansorge et al. | |
| 2007/0099844 | A1 | 5/2007 | Prendergast | |
| 2007/0173524 | A1 | 7/2007 | Prendergast et al. | |

FOREIGN PATENT DOCUMENTS

| DE | 296075 | 11/1991 |
|---|---|---|
| DE | 10155093 | 6/2003 |
| DE | 10330842 | 2/2005 |
| DE | 10337074 | 3/2005 |
| WO | 01/89569 | 11/2001 |
| WO | 02/053169 | 7/2002 |
| WO | 02/053170 | 7/2002 |
| WO | 03/000181 A2 | 1/2003 |
| WO | 03/035067 | 5/2003 |
| WO | 03/045977 | 6/2003 |
| WO | 03/077935 | 9/2003 |
| WO | 2004/004750 | 1/2004 |
| WO | 2004/041820 | 5/2004 |

OTHER PUBLICATIONS

Accession No. 2008:2172 CAPLUS, abstract of Dikusar et al, Russian Journal of General Chemistry (2007), 77(11), 1924-27.*
Hashimoto et al, Bioorganic & Medicinal Chemistry (2002), vol. 10, pp. 461-479.*
Evans et al, IDrugs (2002), vol. 5(6), pp. 577-585.*
Ukhin, L. et al., "Reactions of 2-methylindole with morpholinals of substituted salicylaldehydes", Russian Chemical Bulletin, International Edition, vol. 52, No. 3, pp. 700-704 (2003).
English Language Abstract of DE 103 30 842.
Bugni T. et al. "p-Sulfooxyphenylpyruvic acid from the red macro alga *Ceratodictyon spongiosum* and its sponge symbiont *Haliclona cymaeformis*", Phytochemistry, vol. 60, No. 4, 2002, pp. 361-363.
Ogata M. et al. "Synthesis and Antifungal Activity of a Series of Novel 1,2-Disubstituted Propenones", Journal of Medicinal Chemistry, vol. 30, 1987, pp. 1497-1502.
Boger D. L. et al. "Non-Amide-Based Combinatorial Libraries Derived from N-Boc-Iminodiacetic Acid: Solution-Phase Synthesis of Piperazinone Libraries with Activity Against LEF-1/β-Catenin-Mediated Transcription", Helvetica Chimica Acta, vol. 83, 2000, pp. 1825-1845.

(Continued)

*Primary Examiner* — Kamal Saeed
*Assistant Examiner* — Janet L Coppins
(74) *Attorney, Agent, or Firm* — Abel Law Group, LLP

(57) ABSTRACT

The present invention relates to substances capable of specifically inhibiting Ala-p-nitroanilide-cleaving peptidases and Gly-Pro-p-nitroanilide-cleaving peptidases as well, for a use in the medical field. Furthermore, the invention relates to the use of at least one of such substances or of at least one pharmaceutical or cosmetic composition containing at least one such substance for a prophylaxis or a therapy of diseases, particularly for a prophylaxis and a therapy of diseases accompanied by an excessive immune response (autoimmune diseases, allergies, transplant rejections), of other chronic-inflammatory diseases, of neuronal diseases and cerebral damage, of skin diseases (inter alia acne, psoriasis), of tumor diseases and of specific virus infections (inter alia SARS).

14 Claims, 4 Drawing Sheets

OTHER PUBLICATIONS

Mittal S. et al. "Structure-Activity Relationship of Estrogens: Receptor Affinity and Estrogen Antagonist Activity of Certain (E)- and (Z)-1,2,3-Triaryl-2-propen-1-ones", Journal of Medicinal Chemistry, vol. 28, 1985, pp. 492-497.

Cushman M. et al. "Synthesis and Evaluation of Analogues of (Z)-1-(4-Methoxyphenyl)-2-(3,4,5-trimethoxyphenyl)ethene as Potential Cytotoxic and Antimitotic Agents", Journal of Medicinal Chemistry, vol. 35, 1992, pp. 2293-2306.

Astles P. C. et al. "Selective Endothelin A Receptor Antagonists. 4. Discovery and Structure-Activity Relationships of Stilbene Acid and Alcohol Derivatives", Journal of Medicinal Chemistry, vol. 41, 1998, pp. 2745-2753.

Meanwell N. A. et al. "Nonprostanoid Prostacyclin Mimetics. 4. Derivatives of 2-[3-[2-(4,5-Diphenyl-2-oxazolyl)ethyl]phenoxy]acetic Acid substituted α to the Oxazole Ring", Journal of Medicinal Chemistry, vol. 36, 1993, pp. 3871-3883.

Augustyns K. et al "The Unique Properties of Dipeptidyl-peptidase IV (DPP IV / CD26) and the Therapeutic Potential of DPP IV Inhibitors", Current Medicinal Chemistry, vol. 6, No. 4, 1999, pp. 311-327.

Chen T. et al. "Dipeptidyl Peptidase IV Gene Family", Adv. Exp. Med. Biol., vol. 524, 2003, pp. 79-86.

Duke-Cohan J.S. et al. "Serum High Molecular Weight Dipeptidyl Peptidase IV (CD26) is Similar to a Novel Antigen DPPT-L Released from Activated T Cells", The Journal of Immunology, vol. 156, 1996, pp. 1714-1721.

Lendeckel U. et al. "Role of alanyl aminopeptidase in growth and function of human T cells (Review)", International Journal of Molecular Medicine, vol. 4, 1999, pp. 17-27.

Kähne T. et al. "Dipeptidyl peptidase IV: A cell surface peptidase involved in regulating T cell growth (Review)", International Journal of Molecular Medicine, vol. 4, 1999, pp. 3-15.

De Meester I. et al. "Dipeptidyl Peptidase IV Substrates", Adv. Exp. Med. Biol., vol. 524, pp. 3-17 (2002).

Evans D. M. "Dipeptidyl Peptidase IV Inhibitors", IDrugs, vol. 5, No. 6, 2002, pp. 577-585.

Kontoyiannis D. P. et al. "Aminopeptidase N inhibitors and SARS", The Lancet, vol. 361, 2003, p. 1558.

Fournié-Zaluski et al. "New Selective Aminopeptidase N Inhibtors as Potential Therapeutics" in J. Langner and S. Ansorge, "Ectopeptidase", Kluwer Academic/Plenum Publisher, 2002, pp. 51-94.

Komoda M. et al. "Specific Inhibitor of Puromycin-Sensitive Aminopeptidase with a Homophthalimide Skeleton: Identification of the Target Molecule and a Structure-Activity Relationship Study", Bioorganic & Medicinal Chemistry, vol. 9, 2001, pp. 121-131.

Barrett A. J. et al. Membrane "Alanyl aminopeptidase" and "Aminopeptidase PS" in "Handbook of Proteolytic Enzymes", Academic Press, 1998.

Hashimoto Y. "Structural Development of Biological Response Modifiers Based on Thalidomide" Bioorganic & Medicinal Chemistry, vol. 10, 2002, pp. 461-479.

Database Beilstein XP-002320599, database accession No. 7444296, Chemical Name actinonin; and references cited therein.

Database Beilstein XP-002320600, database accession No. 2121406, and references cited therein.

Abstract of Eckstein Z. et al. "The fungistatic activity of 3,4-dichlorophenoxyacethydroxamic acid on pathogenic fungi in vitro" Bull. acad. polon. sci. ser. sci., chim., geol. et geopraph., 1958, (6), pp. 235-238 (abstract retrieved from STN).

Abstract of Alk'Ewicz J. et al. "Fungistatic activity of some hydroxamic acids" Nature, vol. 180, 1957, pp. 1204-1205 (abstract retrieved from STN).

U.S. Appl. No. 10/575,883 to Ansorge et al., filed Apr. 14, 2006 and entitled "Novel Dipeptidyl Peptidase IV Inhibitors Used for Functionally Influencing Different Cells and Treating Immunological, Inflammatory, Neuronal, and Other Diseases", which is a national stage of International Application PCT/EP2004/011645.

U.S. Appl. No. 10/575,882 to Ansorge et al., filed Apr. 14, 2006 and entitled "Novel Alanyl-Amino Peptidase Inhibitors for Functionally Influencing Different Cells and Treating Immunological, Inflammatory, Neuronal, and Other Diseases", which is a national stage of International Application PCT/EP2004/011643.

Kammuller, M. E. et al., "Structural Requirements for Hydantoins and 2-Thiohydantoins to Induce Lymphoproliferative Popliteal Lymph Node Reactions in the Mouse", Int. J. Immunopharmac., vol. 10, pp. 997-1010, 1988.

A. Steinbrecher et al., "Targeting Dipeptidyl Peptidase IV (CD26) Suppresses Autoimmune Encephalomyelitis and Up-Regulates TGF-β1 secretion In Vivo", J. Immunol. 2001;166:2041-2048.

* cited by examiner

DUAL ALANYL AMINOPEPTIDASE AND DIPEPTIDYL PEPTIDASE IV INHIBITORS FOR FUNCTIONALLY INFLUENCING DIFFERENT CELLS AND FOR TREATING IMMUNOLOGICAL INFLAMMATORY, NEURONAL AND OTHER DISEASES

CROSS-REFERENCE TO RELATED APPLICATIONS

The present application is a U.S. National Stage of International Application No. PCT/EP2004/011644, filed Oct. 15, 2004, which claims priority of German Patent Application No. 103 48 044.7, filed Oct. 15, 2003.

The present invention relates to novel substances capable of simultaneously inhibiting the enzyme dipeptidyl peptidase IV and enzymes having an analogous enzymatic effect as well as the enzyme alanyl aminopeptidase and enzymes having an analogous enzymatic effect. Moreover, the invention describes the use of these dual inhibitors for the prophylaxis and for the therapy of diseases including an excessive immune response and having an inflammatory genesis, of neuronal diseases and cerebral damage as well as of tumour diseases.

Dipeptidyl peptidase IV (DPIV; CD26; EC 3.4.14.5) is an ubiquituously present serine protease specifically catalyzing the hydrolysis of peptides after proline or alanine in the second position of the N-terminal end. The gene family of DPIV having enzymatic activity also includes, inter alia, DP 8, DP 9 and FAP/seprase (T. Chen et al.: Adv. Exp. Med. Biol. 524, 79, 2003). A substrate specificity similar to DPIV is shown by Attractin (mahagony protein) (J. S. Duke-Cohan et al.: J. Immunol. 156, 1714, 1996). Said enzyme is also inhibited by inhibitors effectively inhibiting DPIV.

Aminopeptidase N (APN, CD13, EC 3.4.11.2) belongs to the (also ubiquituously present) group of alanyl aminopeptidases predominantly occurring as a membrane protein of type II, as does the cytosolic soluble alanyl aminopeptidase (EC 3.4.11.14; Puromycin-sensitive aminopeptidase, aminopeptidase PS, encephaline-degrading aminopeptidase). Both peptidases act metal-dependant and catalyse the hydrolysis of peptide bonds after N-terminal amino acids of oligopeptides, in the case of APN with preference for alanine at the N-terminal end (A. J. Barrett et al.: Handbook of Proteolytic Enzymes, Academic Press, 1998). All inhibitors of aminopeptidase N also inhibit the cytosolic alanyl amino-peptidase, while specific inhibitors exist for the cytosolic aminopeptidase (M. Komodo et al.; Bioorg. and Med. Chem. 9, 121(2001).

For both groups of enzymes, important biological functions were demonstrated in different cell systems. This is true for the immune system (U. Lendeckel et al.: Intern. J. Mol. Med. 4, 17, 1999; T. Kahne et al.: Intern. J. Mol. Med. 4, 3, 1999; I. De Meester et al: Advanc. Exp. Med. Biol. 524, 3, 2002; published International Patent Application WO 01/89569 C1; published International Patent Application No. WO 02/053170 A3; International Patent Application No. PCT/EP 03/07199), the neuronal system (published International Patent Application No. WO 02/053169 A2 and German Patent Application No. 103 37 074.9), the Fibroblasts (German Patent Application No. 103 30 842.3), the Keratinozytes (published International Patent Application No. WO 02/053170 A3), die sebaceous gland cells/Sebocytes (International Patent Application No. PCT/EP 03/02356), for tumors as well as for infections by viruses, e.g. corona viruses (D. P. Kontoyiannis et al.: Lancet 361, 1558, 2003).

The capability, of DPIV, of specifically inactivating the incretory hormones GIP and GLP has resulted into the development of a new therapeutic concept for treating glucose metabolism disturbances (D. M. Evans: Drugs 5, 577, 2002).

For both enzyme groups, distinguishable inhibitors are known (Reviews are found in: "D. M. Evans: Drugs 5, 577, 2002"; and "M.-C. Fournie-Zaluski and B. P. Roques; in: J. Langner and S. Ansorge, Ectopeptidases, Kluwer Academic/Plenum Publishers, p. 51, 2002).

The isolated inhibition of the alanyl aminopeptidases and of the dipeptidyl peptidase IV group, but particularly the combined inhibition of both enzyme groups results into a strong inhibition of the DNA synthesis and, thereby, of the cell proliferation in immune cells as well as into a change of the cytokine production, particularly into an induction of the immunoregulatory effective TGF-β1 (published International Patent Application No. WO 01/89569 C1; published International Patent Application No. WO 02/053170 A3). For regulatory T-cells, alanyl aminopeptidase inhibitors effect a strong induction of TGF-β1 (International Patent Application No. PCT/EP 03/07199). By an inhibition of both enzyme systems, a reduction or deceleration, respectively, of acute and chronic cerebral deterioration processes in the neuronal system could be demonstrated (published International Patent Application WO 02/053 169 A3 and German laid-open Patent Application No. 103 37 074.9). It could be shown, too, for Fibroblasts (German laid-open Patent Application No. 103 37 074.9), Keratinocytes (published International Patent Application No. WO 02/053 170 A3) and Sebatocytes (International Patent Application No. PCT/EP 03/02356) that a combined inhibition of alanyl aminopeptidases and dipeptidyl peptidase IV effects an inhibition of the growth and a change of the cytokine production.

Thus, there results the surprising fact that the alanyl aminopeptidases and the dipeptidyl peptidase IV as well as analogously working enzymes perform fundamental central biological functions in several organs and cell systems, and a combined inhibition of both groups of enzymes represents an effective therapeutic principle for the treatment of different diseases which are chronic in most of the cases.

By using accepted animal models, the Inventors could demonstrate that, particularly, the combined administration of inhibitors of both groups of peptidases effects, in fact, also in vivo an inhibition of the growth of different cell systems and a suppression of an excessive immune response, of chronic-inflammatory events as well as of cerebral damage (published International Patent Application WO 01/89569 C1). The administration of single inhibitors resulted into a less intensive effect or into no effect at all.

The results achieved up to now were obtained by using known inhibitors of alanyl aminopeptidases and of dipeptidyl peptidase IV alone, which are described in the literature and are, in part, commercially available, particularly by using combinations of inhibitors of both groups of enzymes.

Surprisingly, in the course of a high-throughput screening of substance data bases, there were now found novel, predominantly non-peptidic low-molecular dual inhibitors for the enzyme groups of the alanyl aminopeptidases and of the dipeptidyl peptidase IV.

Hence, the invention relates to novel substances, inhibiting Ala-p-nitroanilide and Gly-Pro-p-nitroanilide as well specifically and, hence, uniting, within one substance, the capability of inhibiting enzymes of both groups of enzymes.

Moreover, the invention relates to novel substances which, as such or as starting materials for further substances, may be used for a therapy of diseases connected to an excessive immune response (autoimmune diseases, allergies and rejections of transplants, sepsis), of other chronic-inflammatory diseases, neuronal diseases and cerebral damage, diseases of the skin (inter alia acne, psoriasis, tumor diseases and specific virus infections (inter alia SARS).

Specifically, the present invention relates to substances of the general formulae C1 to C16 as well as tautomers and stereoisomers of said compounds of the general formulae C1 to C16, as well as pharmaceutically acceptable salts salt derivatives, tautomers and stereoisomers thereof, for a use in the medical field.

In a specific embodiment, the present invention relates to specific compounds having the specific formulae C1.001 to C16.013 which are covered by the above general formulae C1 to C16, which compounds, as examples and without restricting them to those, are listed in the form of tables, as well as tautomers and stereoisomers of said compounds of the general formulae C1.001 to C16.013, and pharmaceutically acceptable salts, salt derivatives, tautomers and stereo-isomers thereof, for a use in the medical field.

Moreover, the invention relates to pharmaceutical compositions comprising at least one compound having one of the general formulae C1 to C16, optionally in combination with per se known and usual carriers and adjuvants.

Moreover, the invention relates to cosmetic compositions comprising at least one compound having one of the general formulae C1 to C16, optionally in combination with per se known and usual carriers and adjuvants.

Furthermore, the invention relates to the use of at least one compound of one of the general formulae C1 to C16 or of at least one of the above-mentioned pharmaceutical or cosmetic compositions for inhibiting the activity of alanyl aminopeptidases or of analogous enzymes and the activity of dipeptidyl peptidase IV or of analogous enzymes as well, in a manner alone or in combination with other inhibitors of alanyl aminopeptidases or of analogous enzymes and/or other inhibitors of dipeptidyl peptidase IV or of analogous enzymes.

Furthermore, the invention relates to the use of at least one compound of one of the general formulae C1 to C16 or of at least one of the above-mentioned pharmaceutical or cosmetic compositions for topically influencing the activity of alanyl aminopeptidases or of analogous enzymes and the activity of dipeptidyl peptidase IV or of analogous enzymes as well, in a manner alone or in combination with other inhibitors of alanyl aminopeptidases or of analogous enzymes and/or other inhibitors of dipeptidyl peptidase IV or of analogous enzymes.

Moreover, the invention relates to the use of at least one compound of one of the general formulae C1 to C16 or of at least one of the above-mentioned pharmaceutical or optionally also cosmetic compositions for a prophylaxis or therapy of a number of diseases. In particular embodiments, without that this should be interpreted as restricting the invention, compounds of the general formulae C1 to C16 in accordance with the invention, particularly any of the compounds summarized in Tables 1 to 16, more particularly the compounds C1.001 to C16.013, may be used as such, or may be used as starting compounds for further compounds or may be used in combination with inhibitors of DPIV and with inhibitors of analogous enzymes and/or with inhibitors of the alanyl aminopeptidases for a therapy of diseases accompanied by an excessive immune response (auto-immune diseases, allergies and transplant rejections), of other chronic-inflammatory diseases, of neuronal diseases and of cerebral damage, diseases of the skin (inter alia acne and psoriasis), tumor diseases and specific virus infections (inter alia SARS).

Furthermore, the invention relates to the use of at least one compound of one of the general formulae C1 to C16 or of at least one of the above-mentioned pharmaceutical or cosmetic compositions for manufacturing a medicament for inhibiting the activity of alanyl aminopeptidases or of analogous enzymes and the activity of dipeptidyl peptidase IV or of analogous enzymes as well, alone or in combination with other inhibitors of alanyl aminopeptidases or of analogous enzymes and/or other inhibitors of DPIV or of analogous enzymes.

Furthermore, the invention relates to the use of at least one compound of one of the general formulae C1 to C16 or of at least one of the above-mentioned pharmaceutical or cosmetic compositions for manufacturing a medicament for topically influencing the activity of alanyl aminopeptidases or of analogous enzymes and the activity of dipeptidyl peptidase IV or of analogous enzymes as well, alone or in combination with other inhibitors of alanyl aminopeptidases or of analogous enzymes and/or other inhibitors of DPIV or of analogous enzymes.

Furthermore, the invention relates to the use of at least one compound of one of the general formulae C1 to C16 or of at least one of the above-mentioned pharmaceutical or optionally also cosmetic compositions for manufacturing a medicament for a prophylactic and therapeutic treatment of a number of diseases. In particular embodiments, without restricting the invention, the compounds of the general formulae C1 to C16, especially the particularly preferred single compounds C1.001 to C16.013 shown in Tables 1 to 16, may be used, as such or as starting substances for further substances or in combination with inhibitors of DPIV or of analogous enzymes, for manufacturing a medicament for a therapy of diseases associated with an excessive immune response (autoimmune diseases, allergies or transplant rejections), of other chronic-inflammatory diseases, of neuronal diseases and cerebral damage, of skin diseases (inter alia acne and psoriasis, of tumor diseases and of specific virus infections (inter alia SARS).

Moreover, the invention relates to a process for inhibiting the activity of alanyl aminopeptidases and of analogous enzymes and also of the activity of dipeptidyl peptidase IV and of analogous enzymes, alone or in combination with other inhibitors of alanyl aminopeptidases and of analogous enzymes and/or of dipeptidyl peptidase IV and of analogous enzymes, by an administration of at least one compound of the general formulae C1 to C16 or of at least one of the above pharmaceutical or cosmetic compositions in an amount required for an inhibition of the enzymatic activity.

Moreover, the invention relates to a process for topically influencing the activity of alanyl aminopeptidases and of analogous enzymes and also of the activity of dipeptidyl peptidase IV and of analogous enzymes, alone or in combination with other inhibitors of alanyl aminopeptidases and of analogous enzymes and/or of dipeptidyl peptidase IV and of analogous enzymes, by an administration of at least one compound of the general formulae C1 to C16 or of at least one of the above pharmaceutical or cosmetic compositions in an amount required for influencing the enzymatic activity.

Moreover, the invention relates to a process for a prophylaxis and/or therapy of one of the diseases or conditions set forth herein by inhibiting the activity of alanyl aminopeptidases or of analogous enzymes and the activity of dipeptidyl peptidase IV and of analogous enzymes, alone or in combination with other inhibitors of alanyl aminopeptidases or of analogous enzymes and/or other inhibitors of DP IV or of analogous enzymes, by an administration of at least one compound of the general formulae C1 to C16 or of at least one of the above pharmaceutical or cosmetic compositions in an amount required for a prophylactic or therapeutic treatment.

The term "analogous enzymes" as used in the present specification and in the claims relates to enzymes having an enzymatic activity analogous to the one shown by the membrane-located alanyl aminopeptidase or by dipeptidyl peptidase IV. This is applicable, for example, for the cytosolic alanyl aminopeptidase (APN) or for FAP/saprase or for attractin (DP IV). The above term is also explained, in this sense, in the above-referenced textbook "A. J. Barrett et al.; Handbook of Proteolytic Enzymes, Academic Press, 1998".

In the general formulae C1 to C16, the residues Rn, i.e. the residues R1, R2, R3, R4, R5, R6, R7, R8, R9, R10, R11, R12 and R13, in pendent of each other represent a residue selected from the group consisting of hydrogen, unsubstituted or substituted, straight chain or branched $C_1$— to $C_{12}$ alkyl, $C_2$— to $C_{12}$ alkenyl and $C_2$— to $C_{12}$ alkynyl, hydroxy, thiol, $C_1$— to $C_{12}$ alkoxy, $C_1$— to $C_{12}$ alkylthio, unsubstituted or substituted, uncondensed or condensed, aryl and cycloalkyl optionally containing one or several hetero atoms from the group of N, O, P and S, unsubstituted or substituted amino, unsubstituted or substituted carbonyl, unsubstituted or substituted thiocarbonyl and unsubstituted or substituted imino.

In detail, the residues Rn, in embodiments of the invention where they represent unsubstituted straight chain or branched alkyl groups having 1 to 12 carbon atoms, represent in preferred embodiments methyl, ethyl, n-propyl, i-propyl, n-butyl, i-butyl, sec-butyl, tert-butyl, n-pentyl, i-pentyl, sec-pentyl, tert-pentyl, n-hexyl, i-hexyl, 3-methylpentyl, 2-ethylbutyl, 2,2-dimethylbutyl as well as all straight chain and branched isomers for the residues heptyl, octyl, nonyl, decyl, undecyl and dodecyl. In accordance with the invention, particularly preferred from the above-mentioned group are alkyl groups having 1 to 6 carbon atoms; among those, the residues methyl, ethyl, n-propyl, i-propyl, n-butyl, i-butyl, sec-butyl and tert-butyl are even more preferred.

In other embodiments according to the invention, the residues Rn, in cases where they represent unsubstituted straight chain or branched alkenyl groups having 2 to 12 carbon atoms, represent in preferred embodiments vinyl, allyl, 1-butenyl, 2-butenyl and all straight chain and branched residues for the radicals pentenyl, hexenyl, heptenyl, octenyl, nonenyl, decenyl, undecenyl and dodecenyl, also with respect to the position of the C=C double bond. In further embodiments of the invention, the residues Rn may also represent straight chain or branched alkenyl groups having several double bonds. Preferred residues of this group are the butadienyl group and the isoprenyl group. Among the above-mentioned groups, particularly preferred in accordance with the invention are the alkenyl groups having 2 to 6 carbon atoms; of those, the groups vinyl, allyl, 1-butenyl and 2-butenyl are even more preferred.

In other embodiments according to the invention, the residues Rn, in cases where they represent unsubstituted straight chain or branched alkynyl groups having 2 to 12 carbon atoms, represent in preferred embodiments ethynyl, propynyl, 1-butynyl, 2-butynyl and all straight chain and branched residues for the radicals pentynyl, hexynyl, heptynyl, octynyl, nonynyl, decynyl, undecynyl and dodecynyl, also with respect to the position of the C≡C triple bond. Among the above-mentioned groups, particularly preferred in accordance with the invention are the alkynyl groups having 2 to 6 carbon atoms; of those, the groups ethynyl, propynyl, 1-butynyl and 2-butynyl are even more preferred.

In accordance with the invention, straight chain and branched alkyl, alkenyl and alkynyl residues may be substituted in a further embodiment of the invention. The substituent(s) may be positioned at any desired position of the backbone made of carbon atoms and may be selected from the group consisting of halogen atoms as fluorine, chlorine, bromine and iodine, alkyl groups having 1 to 6 carbon atoms, hydroxy groups, alkoxy groups having 1 to 6 carbon atoms in the alkyl residue, thio groups and alkylthio groups having 1 to 6 carbon atoms in the alkyl residue and amino groups which may be unsubstituted or substituted with one or two alkyl residues independently of each other having 1 to 6 carbon atoms.

In further embodiments of the invention, the residues Rn in the general formulae C1 to C16 represent $C_1$— to $C_{12}$ alkoxy residues or $C_1$— to $C_{12}$ alkylthio residues. Also for the $C_1$— to $C_{12}$ alkyl residues of these alkoxy and alkylthio groups, the above definitions of the straight chain and branched alkyl residues are applicable. Particularly preferred are straight chain $C_1$— to $C_6$ alkoxy groups and straight chain $C_1$— to $C_6$ alkylthio groups, and particularly preferred are the residues methoxy, ethoxy, n-propoxy, methylthio, ethylthio and n-propylthio.

In further embodiments of the invention, the residues Rn in the general formulae C1 to C16 may also represent unsubstituted or substituted cycloalkyl residues. In accordance with the invention, the cycloalkyl residues may preferably contain three to eight atoms in the ring and may consist exclusively of carbon atoms or may contain one or several hetero atom(s). Among the purely carbocyclic rings, the residues cyclopentyl, cyclopentenyl, cyclopentadienyl, cyclohexyl, cyclohexenylcyclohexadieny, cycloheptyl, cycloheptenyl, cycloheptadienyl and cycloheptatrienyl are particularly preferred. Examples for hetero atom-containing cycloalkyl residues are, in further embodiments of the invention, the residues tetrahydrofuranyl, pyrrolidinyl, imidazolinidyl, piperidinyl, piperazinyl and morpholinyl. Substituents to these carbocyclic and heterocyclic cycloalkyl residues may be selected from the above group of substituents of linear alkyl groups.

In further embodiments of the invention, the residues Rn in the compounds of the general formulae C1 to C16 may represent uncondensed or condensed aryl residues optionally containing one or several hetero atoms from the group of N, O, P and S. The aryl residues may have one ring or may have several rings and, if having several rings, two rings are preferred. Moreover, one ring may preferably have five, six or seven ring members. In systems consisting of several rings condensed to each other, benzo-condensed rings are particularly preferred, i.e. ring systems wherein at least one of the rings is an aromatic six-membered ring. Particularly preferred are aryl residues purely consisting of carbon atoms, selected from phenyl and naphthyl. Particularly preferred aryl residues containing hetero atoms are, for example, selected from the group consisting of indolyl, cumaronyl, thionaphthenyl, quinolinyl (benzopyridyl), quinazolinyl (benzopyrimidinyl) and quinoxylinyl (benzopyrazinyl).

In another embodiment of the invention, cyclic residues either consisting of one ring or consisting of several rings, either containing carbon atoms exclusively or also containing hetero atoms, either aromatic systems or non-aromatic systems, may be substituted. The substituents may be bound to any position of the ring system, either to a carbon atom or to a hetero atom. They may be selected from the group consisting of halogen atoms as, for example, fluorine, chlorine, bromine and iodine, alkyl groups having 1 to 6 carbon atoms, alkoxy groups having 1 to 6 carbon atoms in the alkyl group, and unsubstituted amino groups or amino groups substituted with one or two alkyl groups having—independent of each other—1 to 6 alkyl groups, as well as from hydroxy, thio, ether and thioether groups.

Moreover, in accordance with the invention, the residues Rn (=R1 to R13) may also represent unsubstituted amino residues (—NH₂) or unsubstituted imino residues (—NH—) or substituted amino residues (—NHR1 or —NR1Rm) or substituted imino residues (—NRm—) as well as hydroxy residues —OH, alkoxy residues OR1, thio residues —SH and alkylthio residues —SR1. Herein, the residues R1 and Rm may have the meanings defined above in detail for the residues Rn, and they may be identical or different.

In accordance with the invention, the residues Rn (=R1 to R13) may also represent unsubstituted or substituted residues containing a phosphorus atom, for example PH₂, PHRk, PRkRI, P(OH)₂, P(OH)(ORk), P(ORk)(ORI), P(O)H₂, P(O)HRk, P(O)RkRI; or may represent unsubstituted oxim residues =NOH, =NORk or hydroxylamino residues —NH(OH) or alkoxy amino residues —NH(ORk). In these residues, the substituents Rk and Rl may have the meanings defined above in detail for R1 to R13 and may be identical or different.

In accordance with the invention, the residues Rn (=R1 to R13) may also represent unsubstituted carbonyl residues (H—(C=O)—) or unsubstituted thiocarbonyl residues (H—(C=S)—) or for substituted carbonyl residues (Rm—(C=O)—) or substituted thiocarbonyl residues (Rm—(C=S)—). In these residues, the substituents Rm of substituted carbonyl residues or substituted thiocarbonyl residues have the meanings defined above for the possible substituents of the residues Rn.

In the compounds of the general formulae C1 to C16, the residues Rn (=R1 to R13) represent, in accordance with the invention, hydrogen, CH₃, CH₂Rk, CHRkRl, CRkRlRm, OH, ORk, NH₂, NHRk, NRkRl, C(O)Rk, C(NH)Rk, C(NRl)Rk, C(S)Rk, PH₂, PHRk, PRkRl, P(O)(OH)₂, P(O)(OH)(ORk), P(O)(ORk)(ORl), P(OH)₃, P(OH)₂ORk, P(OH)(ORk)(ORl), P(ORk)(ORl)(ORm), SH, SRk and CN, wherein the residues Rk, Rl and Rm have the meanings defined up to now for the residues R1 to R13.

In accordance with the invention, the above-mentioned residues Rn (=R1, R2, R3, R4, R5, R6, R7, R8, R9, R10, R11, R12 and/or R13) may be bound to the respective basic structures of the general formulae C1 to C16 via one of their carbon atoms. In an alternative embodiment, it is also possible that the residues Rn are bound to the respective basic structures of the general formulae C1 to C16 via the hetero atom or via one of their hetero atoms.

In several of the general formulae C1 to C16 (for example in the general formulae C1, C6, C7, C12, C13, C14), Y, Y1 and Y2 represent residues bound to the basic structure of the respective formula via a C=Y double bond (or a C=Y1 double bond and/or a C=Y2 double bond). In the formulae where they appear, the groups Y represent—independent of each other—one of the residues O, S or NRn, for example NR3, NR4 or NR5, bound to a carbon atom via a double bond. In the latter residues, the radicals Rn (for example R3, R4, R5) may have the meanings mentioned above, including the meaning "hydrogen". Particularly preferably, Y represents O bound to a carbon atom via a double bond.

In several of the general formulae C1 to C16 (for example in the formulae C8, C9, C10, C15), X, X1, X2 and Z represent residues bound to two different carbon atoms via a C—X single bond each (or via a C—X1 single bond or via a C—X2 single bond) or via a C—Z single bond each. In the general formulae where they appear, the residues X and Z represent—independent of each other—for the residues >NH, >NRn (for example >NR5 or >NR10), —O—, —S— —CH₂—, —CHRn— or —CRn₂—, bound to two different carbon atoms by a single bond each, wherein the residues Rn have the meaning given above, or they represent for the residues >N—, >CH— or >CRn— (for example >CR8— or >CR9—) bound to three different carbon atoms via a single bond each, wherein Rn (for example R8, R9) have the meanings given above.

In the compounds having the general formulae C1, C6, C7, C13, X and Z independent of each other represent residues from the group consisting of hydroxy, thiol, C₁— to C₁₂ alkoxy, C₁— to C₁₂ alkylthio, unsubstituted or substituted, uncondensed or condensed aryl or cycloalkyl optionally containing one or several hetero atoms from the group of N, O, P and S, and Amino (NH₂, NHR1, NR1R2), wherein all above-mentioned meanings of X and Z correspond to the meanings for alkoxy, alkylthio, aryl, cycloalkyl and amino which were defined above in detail for the residues Rn of the general formulae C1 to C16.

In the compounds of the general formula C10, X and Z independent of each other represent >CH—, >CR1— or N; therein, at least one of the groups represents a hetero atom of the basic structure or has one hetero atom; therein, R1 has the meanings defined above.

In the compounds of the general formula C4, X1, X2, X3 and X4 may be identical or different and represent the group >CH— or the group >CR3—, wherein R3 may have the meanings defined above, and Y1, Y2 and Y3 may be identical or different and represent unsubstituted or substituted carbon units or hetero atom units with the ring atoms N, O, P or S.

In accordance with the invention, in the compounds of the general formula C16, A for the exemplifying embodiments 30a and 30b as well as X, Y and Z for the exemplifying embodiment 30a each are an independently selected ring member or part of a ring member in a homocyclic or heterocyclic condensed system consisting of a five-membered and a six-membered ring. A is a part of the five-membered ring, and Y and Z are parts of the five-membered ring. X is a part of the connection of the condensed system. A, Y and Z are selected from the group consisting of CH₂, CHRk, CRkRl, C(O), C(S), C(NH), C(NRk), NH, NRk, =NOH, =NORk, O, S, SO₂, PH, PRk, P(O)OH, P(O)ORk, P(OH)₃, P(OH)₂ORk, P(OH)(ORk)(ORl), P(ORk)(ORl)(ORm).

X represents N, CH, CRk, P, P=O, P(OH)₂, P(OH)(ORk) or P(ORk)(ORl).

The residues Rk, Rl and Rm have the above-defined meanings of the residues Rn (=R1 to R13).

The compounds of the general formulae C1 to C16 (in general) and the compounds C1.001 to C16.013 in Tables 1 to 16 (specifically) may be prepared in accordance with processes known from the literature or are commercially available.

The compounds corresponding to the general formulae C1 to C16 (in general) and the specific compounds C1.001 to C16.013 indicated in Tables 1 to 16 (in preferred embodiments of the invention) are claimed for a use in the medical field. The term "for a use in the medical field" is understood here, and in the claims as well, in its broadest sense and relates to all conceivable fields of application, where the compounds of the general formulae C1 to C16 defined by the present invention, and the compounds C1.001 to C16.013 as mentioned in Tables 1 to 16, in preferred embodiments, may exert an effect in connection to medically relevant conditions of the body of a mammal, in particular of the body of a human.

In connection to such medically relevant conditions, the compounds of the general formulae C1 to C16 (in general) and the preferred compounds C1.001 to C16.013 according to Tables 1 to 16 are used either in the form of a single compound or are used in the form of more than one compound, or several compounds, of the general formulae C1 to C16 (in particular of the compounds C1.001 to C16.013 according to Tables 1 to 16). Also covered by the scope of the present invention is a use of one or more than one compound of the general formulae C1 to C16, preferably of one or more than one compound selected from the group consisting of the compounds C1.001 to C16.013 according to Tables 1 to 16, in combination with other effective agents, for example one or more than one compound having an effect in the inhibition of alanyl aminopeptidases or of analogous enzymes (i.e. of enzymes having an equal substrate specificity) and/or an effect in the inhibition of dipeptidyl peptidase IV (DP IV) or of analogous enzymes (i.e. of enzymes having an equal substrate specificity). Examples of such compounds having an effect as enzyme inhibitor(s) are mentioned in parallel patent applications filed by the Applicants of the present application on the same filing date as the present application as well as in the Applicants' patent applications referred to in the introduction to the present description, the whole disclosed content of which applications is incorporated into the present specification by this reference.

Specific examples of inhibitors effective as inhibitors of dipeptidyl peptidase IV or of analogous enzymes, which are known from the prior art and may optionally be used together with the compounds of the present invention particularly with one or several of the compounds C1.001 to C16.013 according to Tables 1 to 16, include, for example: Xaa-Pro dipeptides, corresponding derivatives, preferably dipeptide phosphonic acid diaryl esters, dipeptide boronic acids (e.g. Pro-bobo-Pro) and their salts, Xaa-Xaa-(Trp)-Pro-(Xaa)n peptides (n=0 to 10), corresponding derivatives and their salts, and amino acid (Xaa) amides, corresponding derivatives and their salts, wherein Xaa is an α-amino acid/imino acid or an α-amino acid derivative/imino acid derivative, preferably $N^\epsilon$-4-nitrobenzyl-oxycarbonyl-L-lysine, L-proline, L-tryptophane, L-isoleucine, L-valine, and cyclic amines as, for example pyrrolidine, piperidine, thiazolidine and their derivatives act as the amide structure. Such compounds and their preparation were described in an earlier patent (K. Neubert et al.; DD 29 60 75 A5). Furthermore, tryptophane-1,2,3,4-tetrahydroisoquinoline-3-carboxylic acid derivatives (TSL) and (2S,2S',2S")-2-[2'-[2"-amino-3"-(indol-3'"-yl)-1"-oxoprolyl]-1',2',3',4'-tetrahydro-6'8'-dihydroxy-7-methoxyisoquinol-3-yl-carbonyl-amino]-4-hydrome-thyl-5-hydropentanoic acid (TMC-2A) may advantageously be used as the effectors for the DP IV together with the compounds of the general formulae C1 to C16. One example of an inhibitor of DP IV preferably useable together with the compounds of the general formulae C1 to C16 is Lys[Z(NO$_2$)] thiazolidide, wherein Lys represents an L-lysine residue an Z(NO$_2$) represents 4-nitrobenzyl-oxycarbonyl (see also DD 29 60 75 A5).

Specific examples of inhibitors effective as inhibitors of alalyl aminopeptidase, which are known from the prior art and may optionally be used together with the compounds of the present invention particularly with one or several of the compounds C1.001 to C16.013 according to Tables 1 to 16, include, for example: actinonine, leuhistine, phebestine, amastatine, bestatine, probestine, β-amino thiols, α-amino phosphinic acids, α-amino phosphinic acid derivatives, preferably D-Phe-ψ-[PO(OH)—CH$_2$]-Phe-Phe. Known alanyl aminopeptidase inhibitors particularly preferred and useable together with the compounds of the present invention are bestatine (Ubenimex), actinonine, probestine, phebestine, RB3014 or leuhistine.

Another embodiment of the present invention relates to pharmaceutical compositions, which comprise at least one, optionally two or even more, compound(s) of the general formulae C1 to C16, particularly preferably selected from the compounds C1.001 to C16.013 according to Tables 1 to 16. Such pharmaceutical compositions comprise one or several of said compounds in such amounts required for exerting a pharmaceutical effect. Such amounts may in detail be determined by a skilled person by a few routine tests and without adding an inventive activity. In general, these amounts are in ranges of from 0.01 to 1000 mg of each of the compounds of the general formulae C1 to C16, particularly preferred of the compounds C1.001 to C16.013 according to Tables 1 to 16, per administration unit, even more preferred in ranges of from 0.1 to 100 mg of each of said compounds per administration unit. Moreover, amounts adjusted to the respective single mammalian organism or human organism may easily be determined by a skilled person, and it may also be provided that a sufficient concentration of the compound(s) to be used may be achieved by an administration of divided or of several administration units.

Another embodiment of the present invention relates to cosmetic compositions, which comprise at least one, optionally two or even more, compound(s) of the general formulae C1 to C16, particularly preferably selected from the compounds C1.001 to C16.013 according to Tables 1 to 16. Such cosmetic compositions comprise one or several of said compounds in such amounts required for exerting a desired effect, for example a cosmetic effect. Such amounts may in detail be determined by a skilled person by a few routine tests and without adding an inventive activity. In general, these amounts are in ranges of from 0.01 to 1000 mg of each of the compounds of the general formulae C1 to C16, particularly preferred of the compounds C1.001 to C16.013 according to Tables 1 to 16, per administration unit, even more preferred in ranges of from 0.1 to 100 mg of each of said compounds per administration unit. Moreover, amounts adjusted to the respective single mammalian organism or human organism may easily be determined by a skilled person, and it may also be provided that a sufficient concentration of the compound (s) to be used may be achieved by an administration of divided or of several administration units.

The one compound or the several compounds according to the present invention or pharmaceutical or cosmetic compositions containing it/them is/are administered simultaneously with known carrier substances and/or auxiliary substances (adjuvants). Such carrier and auxiliary substances are known to a skilled person as such and also with respect to their function and way of application and need no detailed explanation here.

The invention also comprises pharmaceutical compositions which comprise: one or several of the inhibitors of the DP IV or of the inhibitors of enzymes having a DP IV-analogous enzymatic activity and/or the inhibitors of the APN or of the inhibitors of enzymes having an APN-analogous enzymatic activity in accordance with the prior art, together with one or with several compound(s) of the general formulae C1 to C16, particularly preferably together with one or several compound(s) which are selected from the compounds C1.001 to C16.013 of the Tables 1 to 16, in a spaced apart formulation in combination with known carrier substances, auxiliary substances and/or additives for a simultaneous or, with respect to the time, immediately successive administration with the aim of a joint effect.

The administration of the compounds of the general formulae C1 to C16 in general and, preferably, of the compounds C1.001 to C16.013 according to Tables 1 to 16 or the administration of pharmaceutical or cosmetic compositions comprising one or several of the above compounds together with usual carrier substances, auxiliary substances and/or additives, is effected, on the one hand, as a topical application in the form of, for example, creams, ointments, pastes, gels, solutions, sprays, liposomes and nanosomes, lotion, "pegylated" formulations, degradable (i.e. decomposable under physiological conditions) depot matrices, hydrocolloid dressings, plasters, micro-sponges, prepolymers and similar novel carrier substrates, jet injections and other dermatological bases/vehicles including instillative application, and on the other hand, as a systemic application for an oral, transdermal, intravenous, subcutaneous, intracutaneous, intramuscular or intrathecal application in suitable recipes or in suitable galenic forms.

In accordance with the invention, the compounds of the general formulae C1 to C16 in general, and preferably the compounds C1.001 to C16.013 according to Tables 1 to 16, alone or in combination, or pharmaceutical or cosmetic compositions comprising one or several of said compounds are used for an inhibition of the activity of the alanyl aminopeptidases or of analogous enzymes and also for an inhibition of the activity of the dipeptidyl peptidase IV or of analogous enzymes, alone or in combination with other inhibitors of the alanyl aminopeptidases or of analogous enzymes and/or with other inhibitors of the DP IV or of analogous enzymes.

In another embodiment, the compounds of the general formulae C1 to C16 in general, and preferably the compounds C1.001 to C16.013 according to Tables 1 to 16, alone or in combination, or pharmaceutical or cosmetic compositions comprising one or several of said compounds are used for topically influencing the activity of the alanyl aminopeptidases or of analogous enzymes and also for topically influencing the activity of the dipeptidyl peptidase IV or of analogous enzymes, alone or in combination with other inhibitors of the alanyl aminopeptidases or of analogous enzymes and/or with other inhibitors of the DP IV or of analogous enzymes.

In preferred embodiments of the invention, the compounds of the general formulae C1 to C16 in general, and preferably the compounds C1.001 to C16.013 according to Tables 1 to 16, alone or in combination, or pharmaceutical or cosmetic compositions comprising one or several of said compounds are used for a prophylaxis and a therapy of diseases as, for example: multiple sclerosis, Morbus Crohn, Colitis ulcerosa and other autoimmune diseases as well as of inflammatory diseases, of Asthma bronchiale and other allergic diseases, of skin and mucosa diseases, for example psoriasis, acne and dermatologic diseases being accompanied by a hyperproliferation and by changed differentiation states of fibroblasts, of benign fibrosing and sclerosing skin diseases and of malign fibroblastar hyperproliferation states, of acute neuronal diseases as, for example, ischemia-caused cerebral damage after an ischemic or hemorrhagic stroke, craniocerebral trauma, heart arrest, myocardial infarct or as a consequence of heart surgery, of chronic neuronal diseases, for example Morbus Alzheimer, Pick's disease, of the progressive supranuclear palsy, of a corticobasal degeneration, of a frontotemporal dementia, of Morbus Parkinson, particularly of Morbus Parkinson coupled to the chromosome 17, of Morbus Huntington, of disease states caused by prions, and od amyotrophic lateral sclerosis, of artherosclerosis, of arterial inflammations, of a stent restenosis, of chronic obstructive pulmonal diseases (Chronisch Obstruktive Lungenerkrankungen; COPD), of tumors, of metastases, of prostata tumors, of Heavy Acute Respiratory Syndrome (SARS) and of sepsis and sepsis-like conditions.

In a further preferred embodiment of the invention, the compounds of the general formulae C1 to C16 in general, and preferably the compounds C1.001 to C16.013 according to Tables 1 to 16, alone or in combination, or pharmaceutical or cosmetic compositions comprising one or several of said compounds are used for a prophylaxis and a therapy of a rejection of transplanted tissues and cells. As an example of such an application, there may be mentioned the use of one or of several of the above-mentioned compounds of a pharmaceutical composition containing one or several of the said compounds in connection with allogenic or xenogenic transplanted organs, tissues and cells as, for example, kidney transplants, heart transplant, liver transplants, pancreas transplants, skin transplants and stem cell transplants as well as graft versus host diseases.

In a further preferred embodiment of the invention, the compounds of the general formulae C1 to C16 in general, and preferably the compounds C1.001 to C16.013 according to Tables 1 to 16, alone or in combination, or pharmaceutical or cosmetic compositions comprising one or several of said compounds are used for a prophylaxis and a therapy of rejection and inflammation reactions at, or by, medical devices implanted into an organism ("medical devices"). These may comprise, for example, stents, articulation implants (knee joint implants, hip joint implants), bone implants, heart pacemakers, or other implants. In a further preferred embodiment of the invention, the compounds of the general formulae C1 to C16 in general, and preferably the compounds C1.001 to C16.013 according to Tables 1 to 16, alone or in combination, or pharmaceutical or cosmetic compositions comprising one or several of said compounds are used in such a way that the compound(s) or composition(s) is/are applied onto the article or articles in the form of a coating or layer, or at least one of the compounds or compositions is admixed, as a substance, to the material of the article or articles. Also in this case, it is possible—of course—that at least one of the compounds or compositions is administered locally or systemically, optionally successively or parallel in time.

In a similar way as described above, and for similar purposes or for the prophylaxis and therapy of the above diseases and conditions mentioned as examples, however without any restriction, the compounds of the general formulae C1 to C16 in general, and preferably the compounds C1.001 to C16.013 according to Tables 1 to 16, alone or in combination, or the above-mentioned pharmaceutical or cosmetic compositions comprising one or several of said above-mentioned compounds may be used for the preparation of a medicament for a prophylaxis and a therapy of the above-mentioned diseases or conditions. These medicaments may comprise said compounds in the amounts specified above, optionally together with known carrier substances, auxiliary substances and/or additives.

Finally, the invention also relates to a process for inhibiting the activity of the alanyl aminopeptidases or of analogous enzymes and also the activity of dipeptidyl peptidase IV and of analogous enzymes, alone or in combination with other inhibitors of the alanyl aminopeptidases or of analogous enzymes and/or other inhibitors of DP IV or of analogous enzymes by an administration of at least one compound or pharmaceutical or cosmetic composition according to the above detailed description in an amount required for an inhibition of the enzyme activity. The amounts of one of the compounds of the general formulae C1 to C16 in general and of the compounds C1.001 to C16.013 according to Tables 1 to 16 are—as indicated above—in the range of from 0.01 to 1000 mg of one compound per administration unit, preferably in the range of from 0.1 to 100 mg of one compound per administration unit.

The invention also relates to a process for topically influencing the activity of the alanyl aminopeptidases or of analogous enzymes and also the activity of dipeptidyl peptidase IV and of analogous enzymes, alone or in combination with other inhibitors of the alanyl aminopeptidases or of analogous enzymes and/or other inhibitors of DP IV or of analogous enzymes by an administration of at least one compound or pharmaceutical or cosmetic composition according to the above detailed description in an amount required for topically influencing the enzyme activity. Also in these cases, the amounts of said compound(s) are in the above-indicated range.

Furthermore, the invention also relates to a process for the prophylaxis and therapy of a plurality of diseases, for example diseases accompanied by an excessive immune response (autoimmune diseases, allergies, transplant rejections), of other chronically inflammatory diseases, of neuronal diseases and cerebral damage, of skin diseases (inter alia acne and psoriasis) tumor diseases and specific virus diseases (inter alia SARS), and particularly of the above mentioned diseases, by an administration of at least one compound or of a pharmaceutical or cosmetic composition in accordance with the above detailed description in an amount required for the prophylaxis and therapy of the respective disease. Also in these cases, the amounts of the above compound(s) are in the above-mentioned range of from 0.01 to 1000 mg of one compound per administration unit, preferably in the range of from 0.1 to 100 mg of one compound per administration unit.

BRIEF DESCRIPTION OF THE DRAWINGS

The invention will be explained in greater detail below with reference to illustrative, non-limiting embodiments in drawings, in which.

Figure 1:
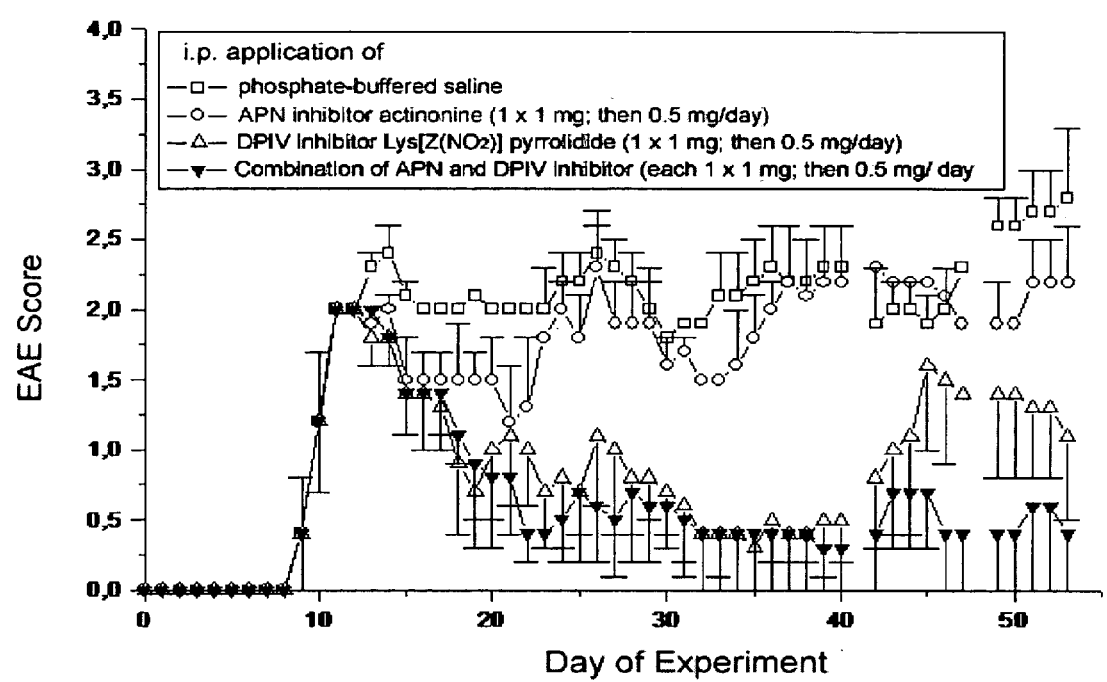
FIG. 1 is a graph showing the effect over time of i.p. application of several substances on the disease scores of mice with EAE as described in Example 2 below.

In the following, the invention is in more detail explained by specific preferred exemplary embodiments. Those exemplary embodiments, however, do not serve a limitation of the invention, but only an exemplifying explanation.

EXAMPLES

Example 1

Inhibition Characteristics of the Novel Dual Inhibitors of the Dipeptidyl Peptidase IV and of the Alanyl Aminopeptidase In the following Tables 1 to 16, novel inhibitos are summarized, for which the inventors could show that these substances are capable of simultaneously inhibiting both peptidases and enzymes having an analog effect in their enzymatic activities. The inhibition characteristics measured are referred to as IC-50 values or ID50 values (the lafter marked with "*") for both enzymes. The enzymatic activity was determined by means of the fluorogenic substrates/products $(Ala-Pro)_2$-rhodamine and $(Ala)_2$-rhodamine.

TABLE 1

| Compound ID. | Structure | IC50$_{DPIV/APN}$ [µM] |
|---|---|---|
| C1.001 | 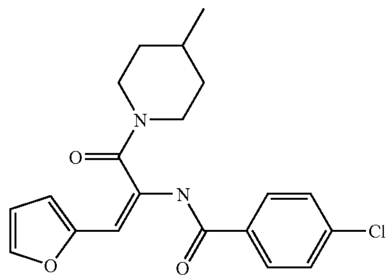 | 18.5/6.2 |
| C1.002 | 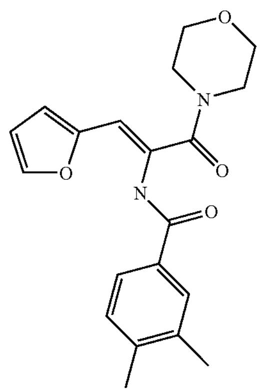 | 46.5/28.8 |
| C1.003 | 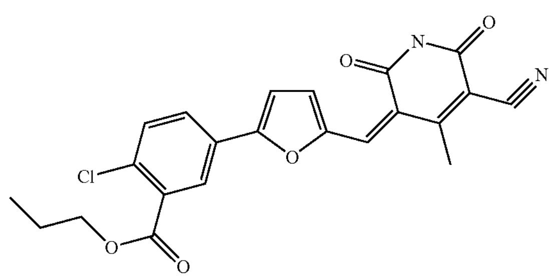 | 65.3/36.8 |

TABLE 2

| Compound ID. | Structure | IC50$_{DPIV/APN}$ [µM] |
|---|---|---|
| C2.001 | 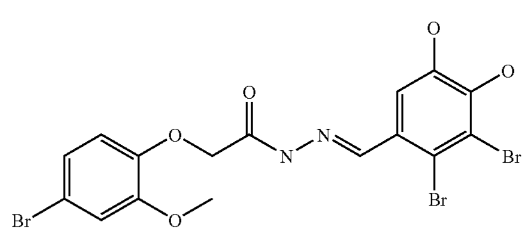 | 10.2/5.0 |

TABLE 2-continued

| Compound ID. | Structure | IC50$_{DPIV/APN}$ [μM] |
|---|---|---|
| C2.002 | 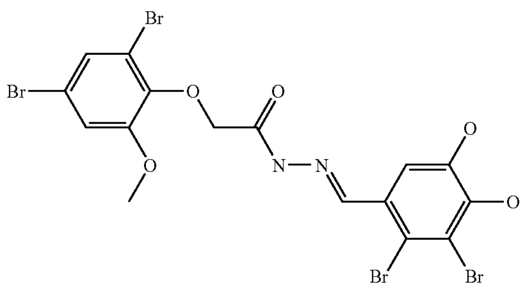 | 9.1/7.2 |
| C2.003 | 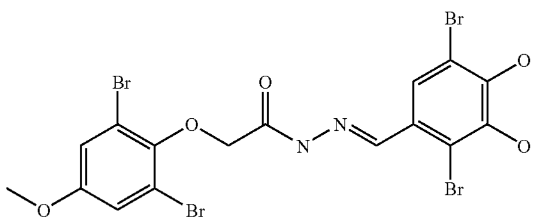 | 29.2/5.4* |
| C2.004 | 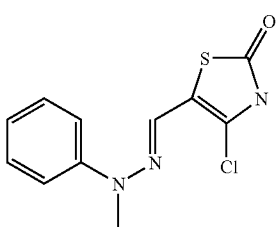 | 32.4/14.4 |
| C2.005 | 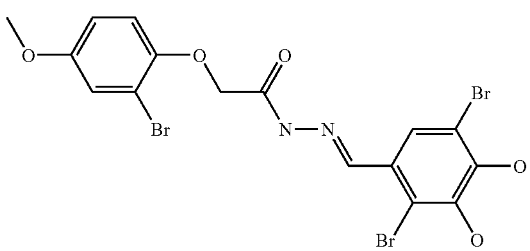 | 40.8/15.0 |
| C2.006 | 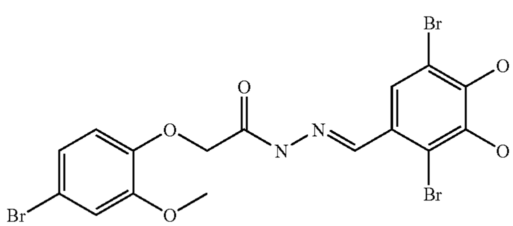 | 45.0/20.5 |
| C2.007 | 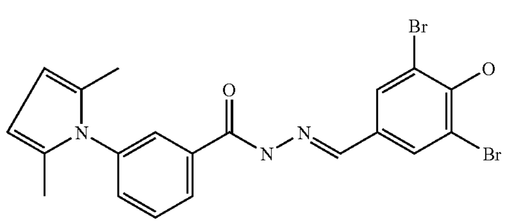 | 41.1/24.9 |
| C2.008 | 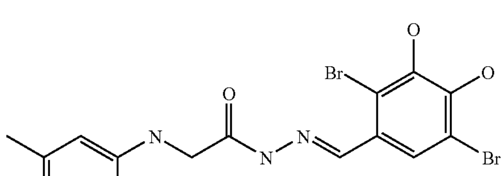 | 65.5*/7.8 |

TABLE 3
| Compound ID. | Structure | IC50$_{DPIV/APN}$ [µM] |
|---|---|---|
| C3.001 | 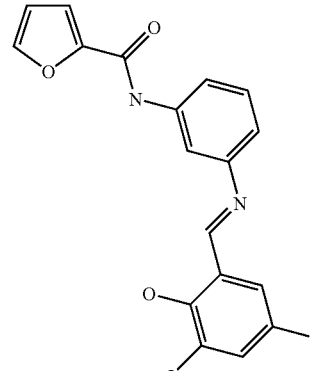 | 2.5*/3.6 |
| C3.002 | 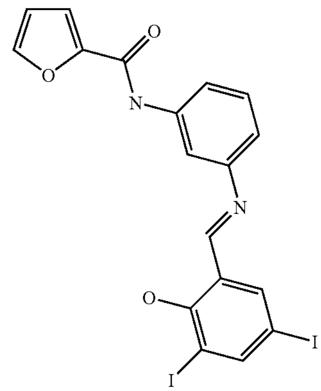 | 9.2/3.0 |
| C3.004 | 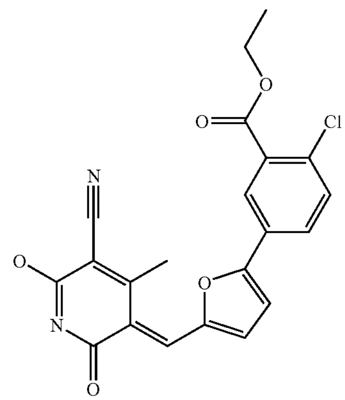 | 56.7/52.1 |
TABLE 4
| Compound ID. | Structure | IC50$_{DPIV/APN}$ [µM] |
|---|---|---|
| C4.002 | 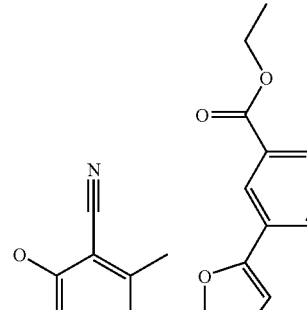 | 12.1/11.8 |
| C4.005 | 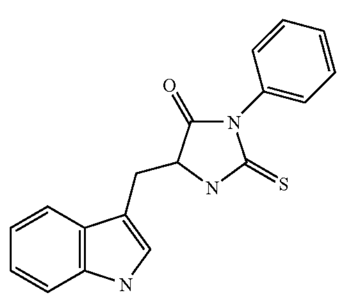 | 40.2/12.4 |

TABLE 4-continued

| Compound ID. | Structure | IC50$_{DPIV/APN}$ [µM] |
|---|---|---|
| C4.006 | 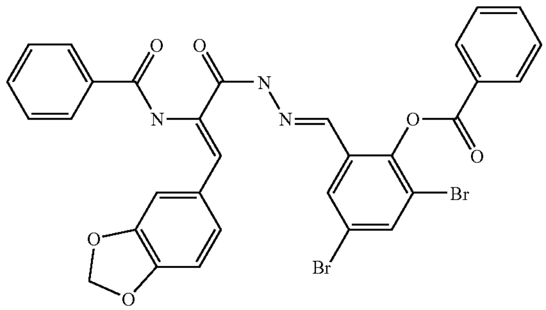 | 38.6/19.8 |
| C4.007 | 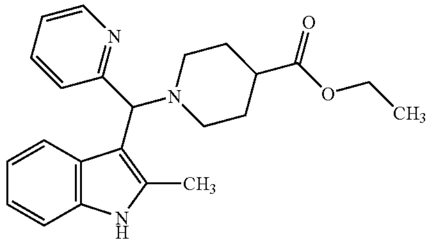 | 32.0/32.0 |
| C4.008 | 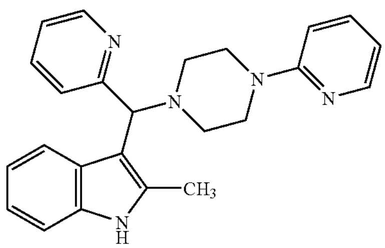 | 45.0/28.0 |
| C4.009 | 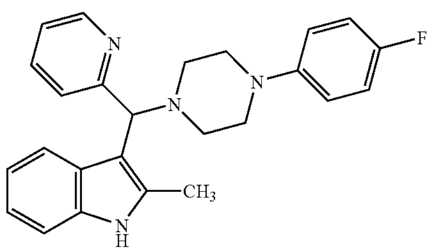 | 96.0/76.0 |
| C4.010 | 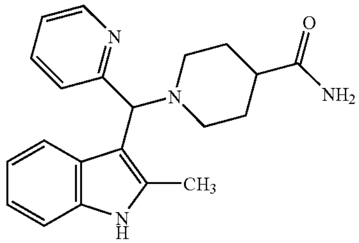 | 54.0/42.0 |
| C4.011 | 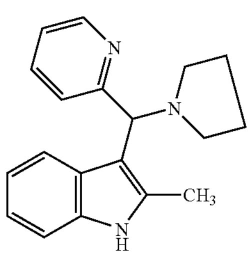 | 170.0/200.0 |
| C4.012 | | 59.0/36.0 |

TABLE 5

| Compound ID. | Structure | IC50$_{DPIV/APN}$ [μM] |
|---|---|---|
| C5.001 | (structure) | 2.5*/3.6 |
| C5.002 | (structure) | 26.2/15.2 |

TABLE 6

| Compound ID. | Structure | IC50$_{DPIV/APN}$ [μM] |
|---|---|---|
| C6.001 | (structure) | 39.5/71.4 |
| C6.002 | (structure) | 59.8/51.3 |

TABLE 7

| Compound ID. | Structure | IC50$_{DPIV/APN}$ [μM] |
|---|---|---|
| C7.001 | (structure) | 18.9/21.7 |
| C7.002 | (structure) | 25.4/48.7 |

TABLE 7-continued

| Compound ID. | Structure | IC50$_{DPIV/APN}$ [μM] |
|---|---|---|
| C7.003 | 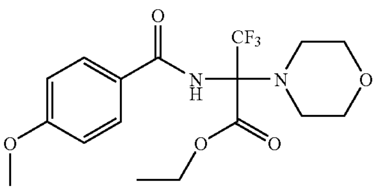 | 29.2/90.2 |
| C7.004 | 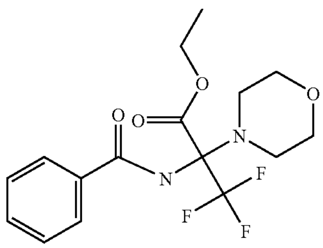 | 61.9/186.0* |

TABLE 8

| Compound ID | Structure | IC50$_{DPIV/APN}$ [μm] |
|---|---|---|
| C8.001 | 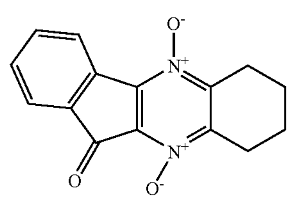 | 14.0/2.0* |
| C8.002 | 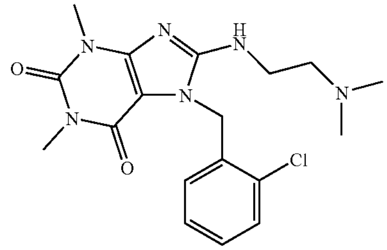 | 7.5/Inactive |
| C8.003 | 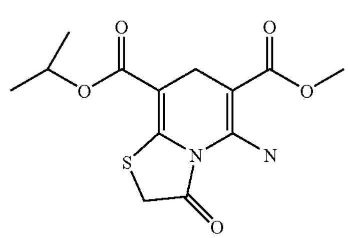 | 10.8/5.9 |

TABLE 8-continued

| Compound ID | Structure | IC50$_{DPIV/APN}$ [μm] |
|---|---|---|
| C8.004 | 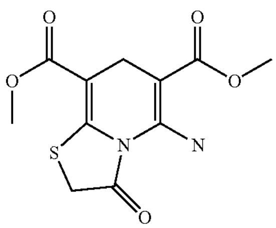 | 34.1/very high positive* |
| C8.005 | 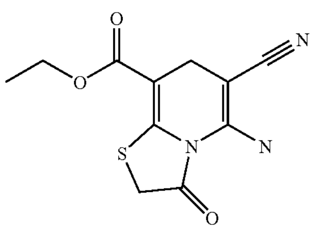 | 14.1/23.1 |
| C8.006 | 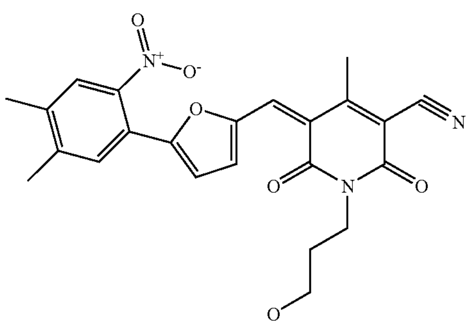 | 34.8/9.7 |
| C8.007 | 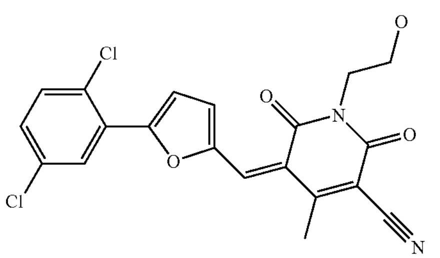 | 51.7/1.2* |
| C8.008 | 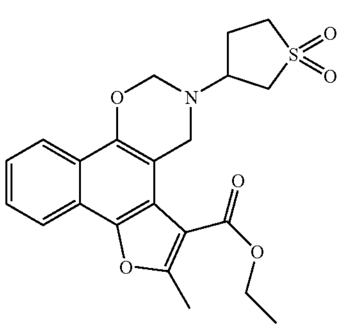 | 34.2/22.3 |
| C8.009 | 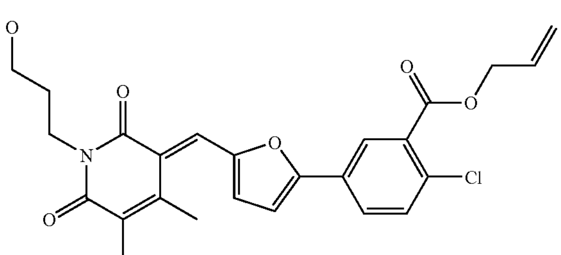 | 44.6/18.1 |

TABLE 9
| Compound ID. | Structure | IC50$_{DPIV/APN}$ [μM] |
|---|---|---|
| C9.001 | 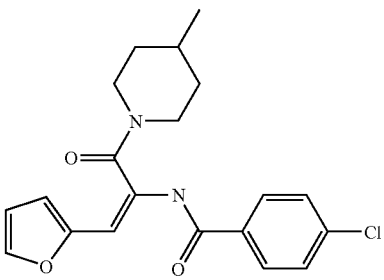 | 18.5/6.2 |
| C9.002 | 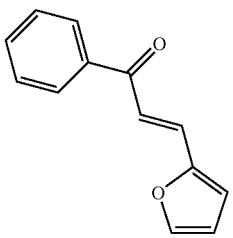 | 19.7/27.3 |
| C9.003 | 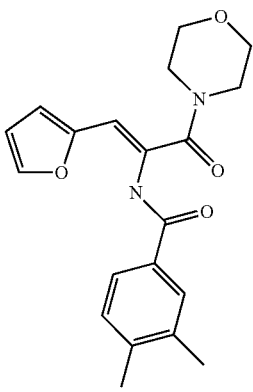 | 46.5/28.8 |
| C9.004 | 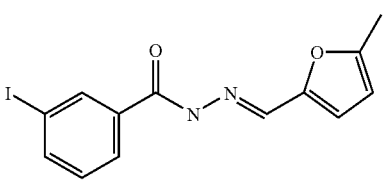 | 57.4/30.0 |
| C9.005 | 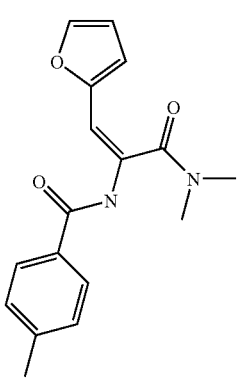 | 47.7/32.5 |

TABLE 9-continued

| Compound ID. | Structure | IC50$_{DPIV/APN}$ [μM] |
|---|---|---|
| C9.006 | 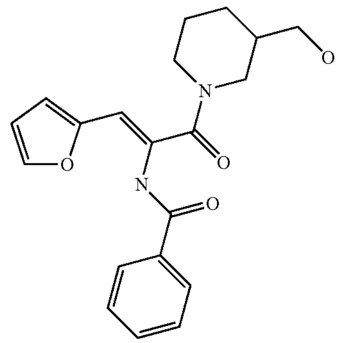 | 152.5/19.0 |

TABLE 10

| Compound ID. | Structure | IC50$_{DPIV/APN}$ [μM] |
|---|---|---|
| C10.003 | 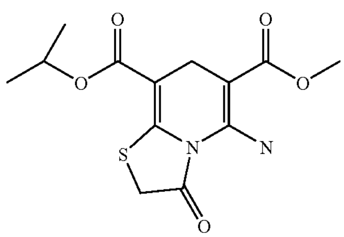 | 10.8/5.9 |
| C10.005 | 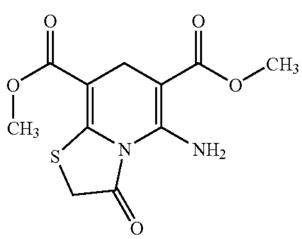 | 34.1/very high positive* |
| C10.012 | 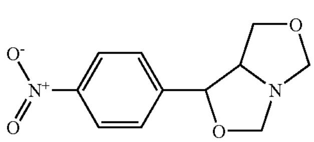 | 42.4/64.5 |
| C10.015 | 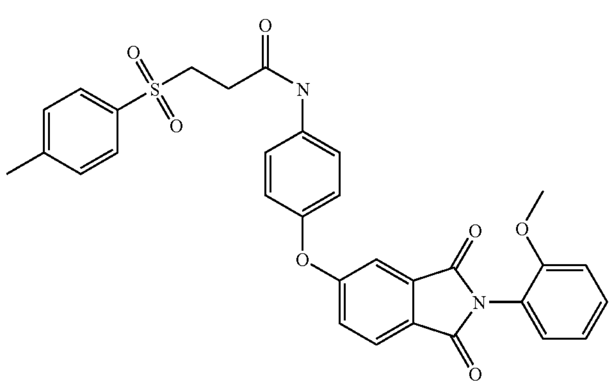 | 99.4/26.7 |

TABLE 11

| Compound ID. | Structure | IC50$_{DPIV/APN}$ [μM] |
|---|---|---|
| C11.001 | 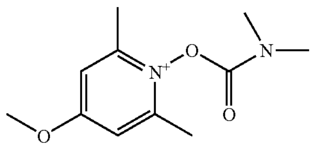 | 118.9*/42.4 |
| C11.002 | 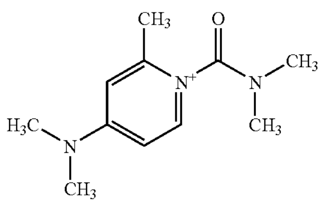 | 283.6*/27.6 |

TABLE 12

| Compound ID. | Structure | IC50$_{DPIV/APN}$ [μM] |
|---|---|---|
| C12.001 | 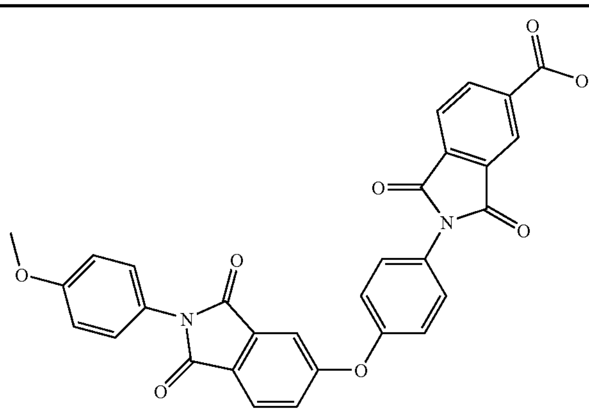 | 20.6/14.8 |

TABLE 13

| Compound ID. | Structure | IC50$_{DPIV/APN}$ [μM] |
|---|---|---|
| C13.001 | 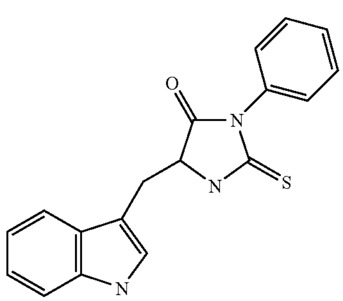 | 40.2/12.4 |
| C13.002 | 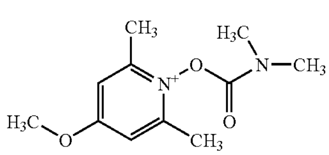 | 118.9*/42.4 |
| C13.003 | | 283.6*/27.6 |

TABLE 14

| Compound ID. | Structure | IC50$_{DPIV/APN}$ [μM] |
|---|---|---|
| C14.001 | 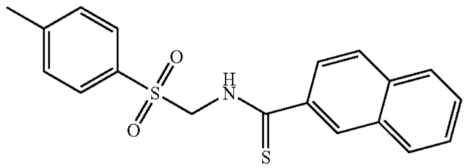 | 14.5/11.8 |
| C14.002 | 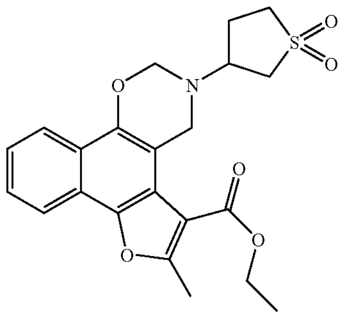 | 34.2/22.3 |

TABLE 15

| Compound ID. | Structure | IC50$_{DPIV/APN}$ [μM] |
|---|---|---|
| C15.002 | 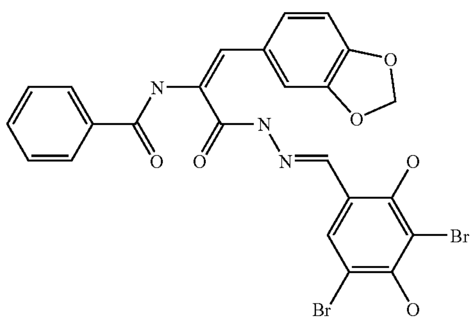 | 60.0/23.6 |
| C15.003 | 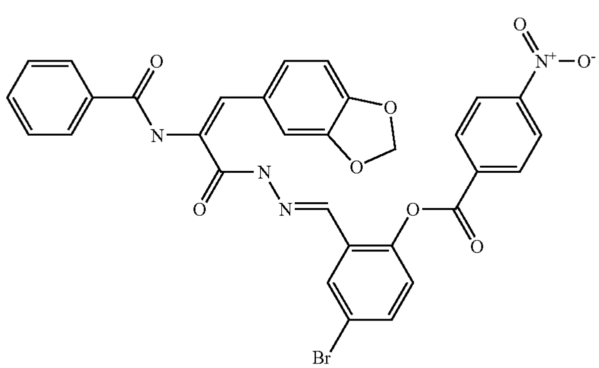 | 271.8*/54.2 |
| C15.004 | 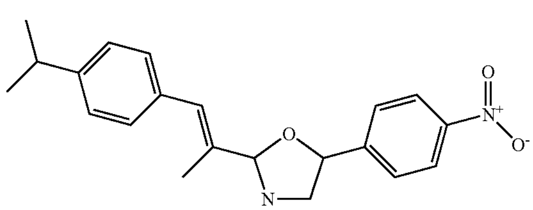 | 65.0/293.0* |

TABLE 16

| Compound ID. | Structure | IC50$_{DPIV/APN}$ [μM] |
|---|---|---|
| C16.001 | 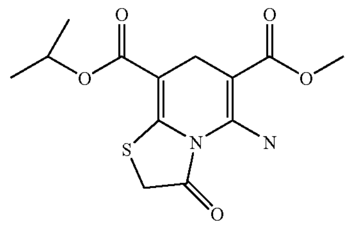 | 10.8/6.9 |
| C16.003 | 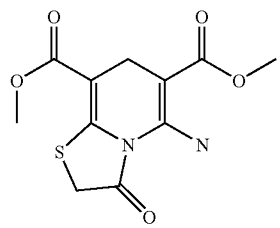 | 34.1/very high positive** |
| C16.004 | 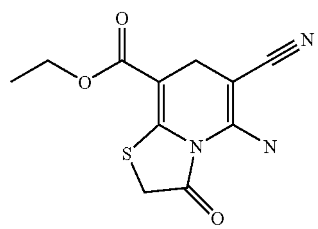 | 14.1/23.1 |
| C16.005 | 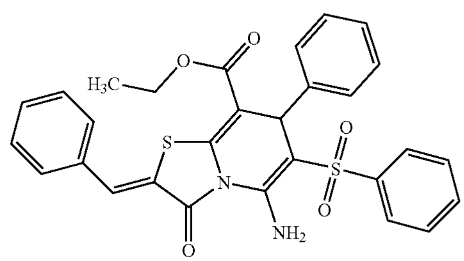 | 200.0/200.0 |
| C16.006 | 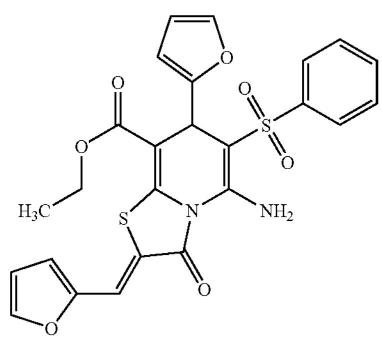 | 200.0/200.0 |
| C16.007 | 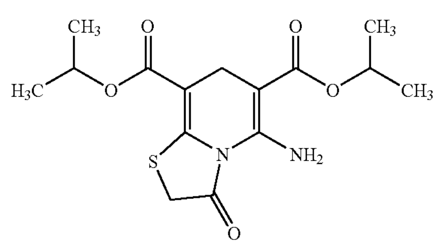 | 79.0/75.0 |
| C16.008 | 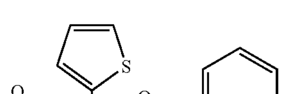 | 139.0/200.0 |

Example 2

Therapeutic Effect of the Combined Inhibition of the Alanyl Aminopeptidases and of Enzymes Having an Analogous Effect as Well as of the Dipeptidyl Peptidase IV and of Enzymes Having an Analogous Effect on the Experimental Autoimmune Encephalomyelitis (EAE) of Mice (Animal Model of Multiple Sclerosis)

The disease EAE was induced by a daily injection of PLP139-151 (myelin antigen proteolipide protein peptide 139-151) to SJL/J mice (n=10). After the outbreak of the disease, there was, on the $11_{th}$ day after the immunization, a therapeutic intervention by an intraperitoneal injection of 1 mg of each of the peptidase inhibitors on the first day and further injections of 0.5 mg of each of the inhibitors on the second day. The disease scores [vD1] are defined by differently distinct degrees of paralysis. Healthy animals have the disease score 0. Actinonine was used as the alanyl aminopeptidase inhibitor, Lys[Z(NO$_2$)] pyrrolidide was used as the dipeptidyl peptidase IV inhibitor. The treatment was effected for the time of 46 days after the immunization. The results are shown in FIG. 1. The course of the curves demonstrate unequivocally a particularly strong and long-lasting [vD2] therapeutic effect after a combined inhibition of both peptidases.

Example 3

Therapeutic Effect of the Combined Inhibition of the Alanyl Aminopeptidases and of Enzymes Having an Analogous Effect as Well as of the Dipeptidyl Peptidase IV and of Enzymes Having an Analogous Effect on the Dextran Sulfate-Induced Colitis of Mice (Animal Model of Chronical Inflammatory Intestinal Diseases)

Figure 2:
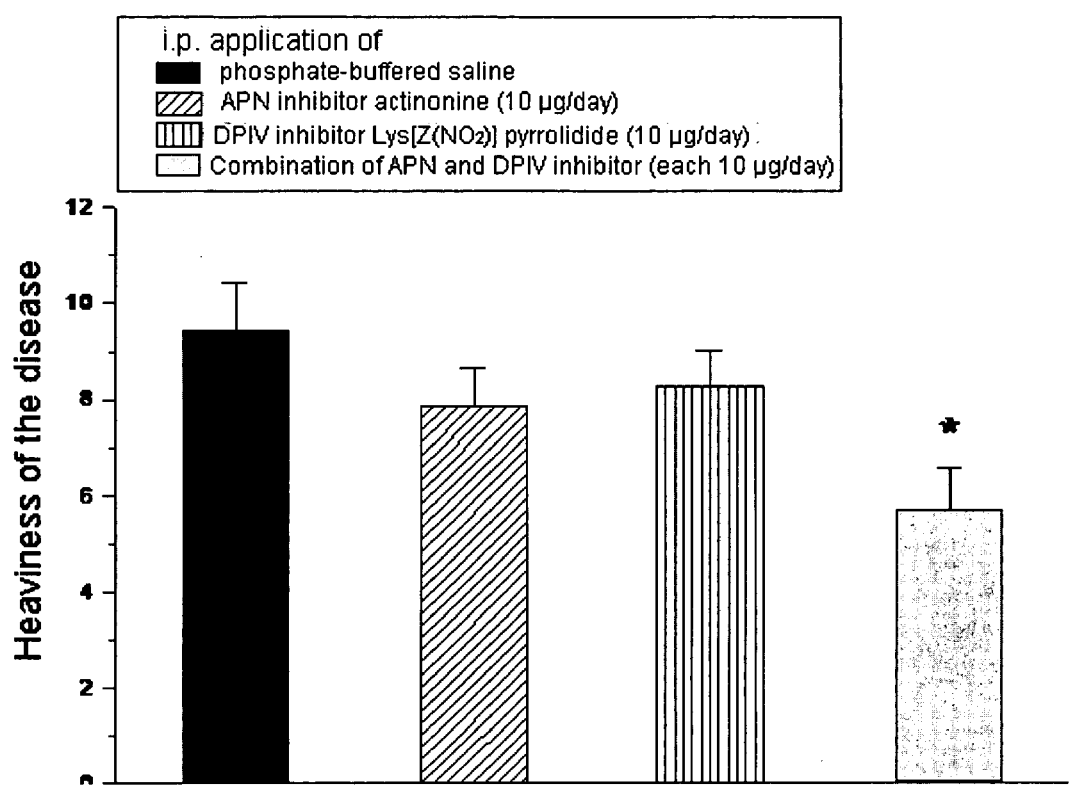
FIG. 2 shows the effect of i.p. application of several substances on the heaviness of the disease scores of mice with inflammation relating predominantly to the colon as described in Example 3 below.

An inflammation relating predominantly to the colon (equivalent to the disease of human Colitis ulcerosa) was induced by an administration of 3% sodium dextran sulfate dissolved in the drinking water of female Balb/c mice having an age of 8 weeks. After three days, all animals showed clear symptoms typical for the disease. The peptidase inhibitors (or phosphate-buffered saline as a placebo) were administered intraperitoneally from day 5 on three successive days. The degree of the disease is determined in accordance with a acknowledged evaluation system (score). The following parameters are considered when determining the score: Consistency of the excrements (solid=0 points (pts.); pasty=2 pts.; liquid/like diarrhea=4 pts.); detection of blood in the excrements (no blood=0 pts.; occult blood=2 pts.; evident=4 pts.); loss of weight (0-5%=0 pts.; 5 to 10%=1 pts.; 10-15%=2 pts.; 15-20%=3 pts.; >20%=4 pts.). Healthy animals have a score value of 0 pts.; the maximum value are 12 pts. From 10 pts. on, the disease is lethal. In the course of the disease, the score value increases due to the change of the excrement parameters. Later-on (starting from day 5), the loss of weight increases the score. FIG. 2 shows the disease intensity for untreated and treated animals on the day 7 after three days of therapy.

The application of 10 µg of the respective single prior art inhibitors (n=14 per group) achieved a slight, but insignificant reduction of the heaviness of the disease (−16.5% by a treatment with actinonine; −12.3% by a treatment with Lys [Z(NO$_2$)] pyrrolidide). An i.p. application of a combination of the two peptidase inhibitors resulted into a statistically significant (p=0.00189) improvement of the disease by 40%.

Example 4

Figure 3:
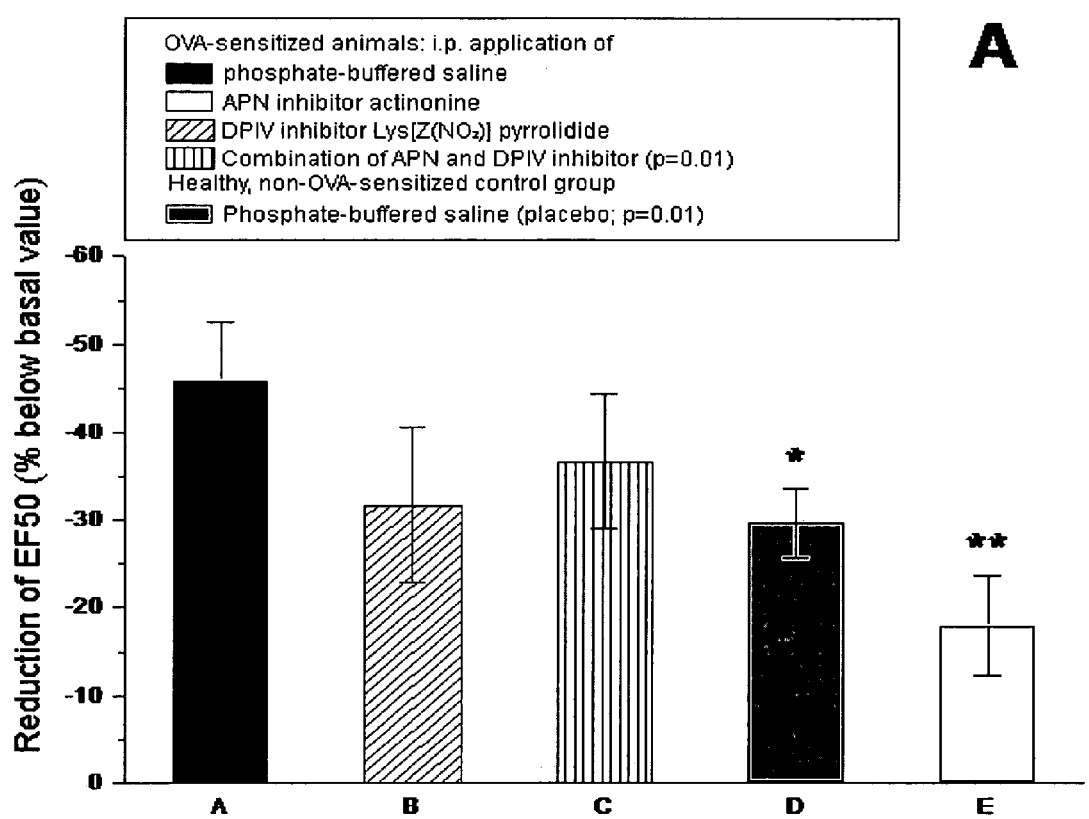
FIG. 3A shows the effect of i.p. application of several substances on the reduction of the average expiratory flux (EF 50) in mice having asthma bronchiale as described in Example 4 below.
FIG. 3B shows the effect of i.p. application of several substances on the reduction of eosinophilia in mice having asthma bronchiale as described in Example 4 below.
Figure 3:
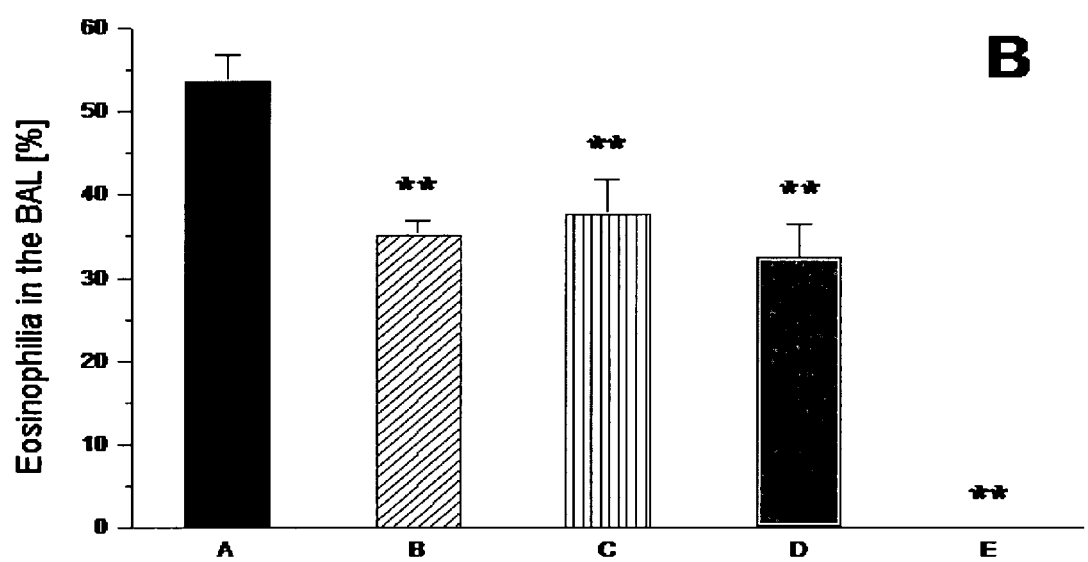

Therapeutic Effect of the Combined Inhibition of the Alanyl Aminopeptidases and of Enzymes Having an Analogous Effect as Well as of the Dipeptidyl Peptidase IV and of Enzymes Having an Analogous Effect on the Ovalbumine-Induced Asthma Bronchiale of Mice (Animal Model of Human Asthma Bronchiale). FIG. 3 Shows the Influence of the Combined Peptidase Inhibition on the Reduction of the Average Expiratory Flux (EF 50) as a Measure of the Pulmonal Function (FIG. 3 A) as Well as on the Eosinophilia as a Characteristic Feature of the Astma Bronchiale Pulmonal Inflammation (FIG. 3B)

Female Balb/c mice were sensitized for the antigen ovalbumine capable of inducing asthma bronchiale by an intreperitoneal administration of 10 µg ovalbumine on the days 0, 14 and 21. On day 27/28, the animals received a boostering dose of ovalbumine by inhalation [vD3]. After an intreperitoneal administration of the peptidase inhibitors on the days 28-35, there was effected an intranasal ovalbumine challenge on day 35, as well as a check of the allergic premature reaction via the pulmonal function. There were measured: the average expiratory flux (EF50), the tidal volume, the respiration rate and the minute volume as well as the number of eosinophilic granulocytes in the bronchoalveolar lavage. 8 to 10 animals were used per experimental group. By way of example, in FIG. 3A, there is summarized the effect of the peptidase inhibitors on the reduction of the EF50 value. The alanyl aminopeptidase inhibitor actinonine (group B; 0.1 mg), and the dipeptidyl peptidase IV inhibitor Lys[Z(NO$_2$)] pyrrolidide as well (group C; 0.1 mg), showed a therapeutic effect. Significant therapeutic effects, however, were obtained only when using combinations of both inhibitors (group D; 0.1 mg of each of the inhibitors [vD4].

Group E represents animals which were not sensitized by OVA, but which were subjected—beyond that—all procedures to which the animal groups A to D were subjected. Hence, this group is a group of healthy, non-allergic animals allowing to calculate stress-induced effects on the pulmonal functions.

What is claimed is:
1. A pharmaceutical or cosmetic composition comprising at least one of a pharmaceutically or cosmetically acceptable carrier and a pharmaceutically or cosmetically acceptable adjuvant and at least one active ingredient selected from a compound of formula:

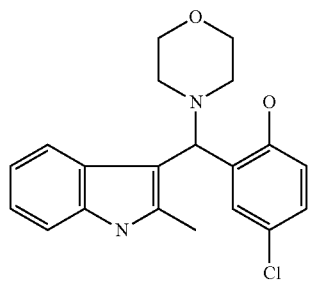

and pharmaceutically acceptable salts thereof.

2. A method of inhibiting an activity of at least one enzyme selected from alanyl aminopeptidases, dipeptidyl peptidase and analogous enzymes in a subject in need thereof, wherein the method comprises administering to the subject the composition of claim 1 in an amount sufficient for inhibiting the activity of the at least one enzyme.

3. A method of treating at least one condition selected from Morbus Crohn, Colitis ulcerosa, rheumatoid arthritis; allergic asthma bronchiale, allergic rhinitis, food allergy, atopic eczema, contact dermatitis, urticaria, angioedema; dermatological diseases associated with a hyperproliferation and changed differentiation states of fibroblasts; and chronic obstructive pulmonal disease (COPD) in a subject in need thereof, wherein the method comprises administering to the subject the composition of claim 1 in an amount sufficient for treating the at least one condition.

4. A method of treating at least one condition selected from atherosclerosis, arterial inflammation, reperfusion syndrome and stent restenosis in a subject in need thereof, wherein the method comprises administering to the subject the composition of claim 1 in an amount sufficient for treating the at least one condition.

5. The method of claim 4, wherein the method comprises administering the composition by using a stent which is coated with the at least one of a composition and an active ingredient thereof.

6. A method of treating an inflammation reaction at, or caused by, a medical device implanted into an organism, wherein the method comprises administering to the organism the composition of claim 1 in an amount sufficient for treating the inflammation reaction.

7. The method of claim 6, wherein the method comprises administering the composition at least one of as a coating or layer on the medical device and incorporated in the medical device.

8. The method of claim 6, wherein the method comprises administering the composition by at least one of a local and a systemic administration successively or concurrently.

9. A method of treating multiple sclerosis in a subject in need thereof, wherein the method comprises administering to the subject the composition of claim 1 in an amount sufficient for treating multiple sclerosis.

10. The method of claim 3, wherein the at least one condition comprises Colitis ulcerosa.

11. The method of claim 3, wherein the at least one condition comprises allergic asthma bronchiale.

12. The method of claim 3, wherein the at least one condition comprises chronic obstructive pulmonal disease (COPD).

13. The method of claim 4, wherein the at least one condition comprises atherosclerosis.

14. The method of claim 4, wherein the at least one condition comprises arterial inflammation.

\* \* \* \* \*